US009599595B2

(12) United States Patent
Gellert

(10) Patent No.: US 9,599,595 B2
(45) Date of Patent: Mar. 21, 2017

(54) COMPREHENSIVE TWO-DIMENSIONAL GAS CHROMATOGRAPH AND MODULATOR FOR THE CHROMATOGRAPH

(71) Applicant: Udo Gellert, Bellheim (DE)

(72) Inventor: Udo Gellert, Bellheim (DE)

(73) Assignee: Siemens Aktiengesellschaft, Munich (DE)

( * ) Notice: Subject to any disclaimer, the term of this patent is extended or adjusted under 35 U.S.C. 154(b) by 508 days.

(21) Appl. No.: 14/018,174

(22) Filed: Sep. 4, 2013

(65) Prior Publication Data

US 2014/0060151 A1     Mar. 6, 2014

Related U.S. Application Data

(60) Provisional application No. 61/696,990, filed on Sep. 5, 2012.

(30) Foreign Application Priority Data

Sep. 5, 2012  (EP) .................................... 12183064

(51) Int. Cl.
*G01N 30/90* (2006.01)
*G01N 30/60* (2006.01)
(Continued)

(52) U.S. Cl.
CPC ....... *G01N 30/6034* (2013.01); *G01N 30/463* (2013.01); *G01N 30/465* (2013.01); *G01N 35/1097* (2013.01)

(58) Field of Classification Search
CPC ......... G01N 30/6095; G01N 2030/025; G01N 30/30; G01N 30/463; G01N 30/60;
(Continued)

(56) References Cited

U.S. PATENT DOCUMENTS 4,891,120 A * 1/1990 Sethi .................. G01N 30/6086
                                                            204/600
4,935,040 A * 6/1990 Goedert ................. G01N 30/20
                                                            210/198.3
(Continued)

FOREIGN PATENT DOCUMENTS

CN          1032588          4/1989

OTHER PUBLICATIONS

"A Review of Basic Concepts in Comprehensive Two-Dimensional Gas Chromatography", Ruby C.Y. Ong and Philip J. Marriott, in Journal of Chromatographic Science, 40 (2002) 276-291.
(Continued)

*Primary Examiner* — Eric S McCall
*Assistant Examiner* — Mohammed E Keramet-Amircolai
(74) *Attorney, Agent, or Firm* — Cozen O'Connor

(57) ABSTRACT

A modulator for simply providing fast and precise sampling of a chromatographic peak eluting from a first column into a second column of a comprehensive two-dimensional gas chromatograph, where the modulator includes a planar component containing a first gas passage for connecting a carrier gas source to the second separation column, a second gas passage for connecting the first separation column to an exhaust outlet, a connecting gas passage between the first and second gas passages, and two individually controllable open/close valves arranged in parallel connection in the first gas passage between its connection to the carrier gas source and the branch-off of the connecting gas passage, and where the gas passages and valves are formed in the planar component by micromachining.

15 Claims, 3 Drawing Sheets

(51) Int. Cl.
*G01N 35/10* (2006.01)
*G01N 30/46* (2006.01)

(58) Field of Classification Search
CPC ........ G01N 30/02; G01N 30/00; G01N 30/74;
G01N 30/88; G01N 2030/027; G01N
30/6034; A61K 2300/00
USPC ........ 73/23.22, 23.35, 61.52, 862.472, 23.39
See application file for complete search history.

(56) References Cited

U.S. PATENT DOCUMENTS

| | | | |
|---|---|---|---|
| 6,447,581 B2 | 9/2002 | Gellert et al. | |
| 2001/0039880 A1 | 11/2001 | Gellert et al. | |
| 2005/0109079 A1* | 5/2005 | Furukawa | G01N 30/20 73/23.42 |
| 2005/0123452 A1* | 6/2005 | Mueller | G01N 30/40 422/89 |
| 2006/0144237 A1* | 7/2006 | Liang | G01N 30/6095 96/101 |
| 2007/0023719 A1 | 2/2007 | Shannon et al. | |
| 2007/0095126 A1* | 5/2007 | Bailey | G01N 30/88 73/23.35 |
| 2009/0150087 A1* | 6/2009 | Steinecker | G01N 30/461 702/24 |
| 2009/0272270 A1* | 11/2009 | McGill | B01J 20/205 96/101 |
| 2010/0154511 A1* | 6/2010 | Lambertus | G01N 30/463 73/25.03 |
| 2010/0162791 A1* | 7/2010 | Breviere | G01N 1/40 73/23.31 |

OTHER PUBLICATIONS

Gwen, M. Gross et al., "High-Speed Gas Chromatography Using Synchronized Dual-Valve Injection", Analytical Chemistry, vol. 76; pp. 3517-3524; 2004.
Firor Roger L. "Comprehensive Flow Modulated Two-Dimensional Gas Chromatography System—Application Brief", pp. 1-4; Agilent Technologies; 2007.
Peter Quinto Tranchida et al. "A Flexible Loop-Type Flow Modulator for Comprehensive Two Dimensional Gas Chromatography", pp. 3140-3145; ISSN 0021-9673 D0I:10.1016/j.chroma.2010.11.082; Journal of Chromatography A vol. 1218; 2011; May 1, 2011.

* cited by examiner

COMPREHENSIVE TWO-DIMENSIONAL GAS CHROMATOGRAPH AND MODULATOR FOR THE CHROMATOGRAPH

CROSS-REFERENCE TO RELATED APPLICATIONS

This is a U.S. non-provisional application and claims priority to U.S. Provisional Application Ser. No. 61/696,990 filed Sep. 5, 2012 and European Application No. 12183064 filed Sep. 5, 2013, the content of which are incorporated herein by reference in their entirety.

BACKGROUND OF THE INVENTION

1. Field of the Invention

The invention relates to a comprehensive two-dimensional gas chromatograph having a first separation column, a second separation column and a modulator controlled by a controller for sampling a chromatographic peak eluting from the first column into the second column.

The invention further relates to a modulator for such a chromatograph.

2. Description of the Related Art

A "Review of the Basic Concepts of Comprehensive Two-Dimensional Gas Chromatography" is provided by Ruby C. Y. Ong and Philip J. Marriott in Journal of Chromatographic Science, 40 (2002) 276-291.

Comprehensive two-dimensional gas chromatography (GC×GC) has to be distinguished from multidimensional or heart-cut gas chromatography (GC–GC), where two separation columns are connected by a valve that allows an introduction of a selected fraction (heart cut) of the eluate from the first column (first dimension) into the second column (second dimension) for further separation and detection. The selected fraction may be a chromatographic peak that emerges from the first column and contains analytes that have not yet been fully separated.

In comprehensive two-dimensional gas chromatography, the entire sample is ideally independently separated in the two separation columns that are connected sequentially with a modulator positioned between them. Typically, the first dimension is a conventional column and the second dimension is a short, fast-elution column. The modulator serves to focus the effluent from the first column in short plugs and to inject them in the second column for rapid separation. There are different types of modulators, some of them are based on temperature differences and others on valve operation.

In cryogenic modulators, for example, the analytes that appear at the end of the first column are collected and concentrated in a cooled region (trap) and released to the second column by heating this region. This allows the sample and transfer of complete chromatographic peaks eluting from the first column.

Valve-based modulators advantageously work without cooling and heating and can be used for fast peaks because they operate at a relatively high frequency. They are simpler, smaller, more rugged and less costly as thermal modulators. Valve-based modulators usually sample less than the complete chromatographic peak because they vent the effluent from the first column to a certain extent so that portions of the effluent will get lost. However, if the peak is short, it may be transferred as a whole by collecting the eluate coming from the first column into a sampling loop and then switching a valve and injecting the content of the sampling loop into the second column at a very high flow rate, a technique that is known for injecting a sample volume into a gas chromatograph. To this end, the modulator may include a six-port valve which, in a first position, connects the sampling loop in line with the first column and an exhaust and, in a second position, connects the sampling loop in line with a carrier gas source and the second column.

Following Gwen M. Gross et al. "High-Speed Gas Chromatography Using Synchronized Dual-Valve Injection", Analytical Chemistry 76 (2004) 3517-3524 who disclose an injection system for high-speed gas chromatography, the above mentioned modulator can be modified by arranging a further six-port valve between the first valve and the second column. The second valve in its first position connects either the carrier gas source (first valve in first position) or the sampling loop (first valve in second position) to the second column. In its second position, the second valve connects the second column to the carrier gas source and the sampling loop to an exhaust (first valve in second position). Thus, it is possible to obtain a sharp, fast and accurate injection pulse that far exceeds the pulse width provided by a single valve. Because the high-speed valves actuate independently, the injection pulse width can be varied depending upon the separation requirements. However, high-speed six-port diaphragm valves are expensive, complex in design and may cause flow disturbances on switching.

From U.S. Pat. No. 6,447,581 B2 a gas flow switching device is known that allows valve-less injection of a sample into a separation column. The device comprises a planar component in which different gas passages are formed by micro-machining techniques in the broadest sense. A first gas passage is at one end connected to a carrier gas source via a capillary and a solenoid valve and at the other end connected to the separation column. A second gas passage receives at one end the sample via a capillary from a sampling loop and opens at the other end to an exhaust capillary. The first and second gas passages a connecting gas passage between the first and second gas passages communicate with one another via a connecting gas passage. When the solenoid valve is open, carrier gas flows through the first gas passage to the separation column, Here, a small percentage of the carrier gas flows into the connecting gas passage and keeps the sample flowing in the second gas passage away from the first gas passage and the column. When the solenoid valve is closed for a short time, the sample is diverted from the second gas passage into the connecting gas passage and reaches the separation column via the first gas passage.

As mentioned above, valve-based modulators and two-dimensional gas chromatographs vent the effluent from the first column to a certain extent so that portions of the effluent will get lost. In order to minimize the corrupting influence of the missing effluent, the peak from the first column is preferably sampled at several times into the second column so that several slices of each peak are delivered to the second column. This requires very fast switching and short delays, such as an injection pulse width of less than 3 ms and an injection cycle time of less than 9 ms.

SUMMARY OF THE INVENTION

It is therefore an object of the invention to provide in a simple manner a fast and precise sampling of a first dimension peak in two-dimensional gas chromatography.

This and other objects and advantages are achieved in accordance with the invention by a two-dimensional gas chromatograph or modulator, where a comprehensive two-dimensional gas chromatograph includes a first separation column, a second separation column and a modulator controlled by a controller for sampling a chromatographic peak eluting from the first column into the second column, where the modulator comprises a planar component containing a first gas passage having a first inlet end to which a carrier gas source is connected and a first outlet end to which the second separation column is connected, a second gas passage having a second inlet end to which the first separation column is connected and a second outlet end, a connecting gas passage between the first and second gas passages, two individually controllable open/close valves arranged in parallel connection in the first gas passage between the first inlet port and the branch-off of the connecting gas passage, where the gas passages and valves are formed in the planar component by micromachining, and where the controller is configured to start each sample event by controlling one of the valves from open to close when the other valve is closed and to stop the sample event by controlling the other valve to open.

It is also an object of the invention to provide a modulator for sampling a chromatographic peak eluting from a first separation column into a second separation column of a comprehensive two-dimensional gas chromatograph, where the modulator comprises a planar component containing a first gas passage having a first inlet end for the connection of a carrier gas source and a first outlet end for the connection of the second separation column, a second gas passage having a second inlet end for the connection of the first separation column and a second outlet end, a connecting gas passage between the first and second gas passages, two individually controllable open/close valves arranged in parallel connection in the first gas passage between the first inlet port and the branch-off of the connecting gas passage, and the gas passages and valves being formed in the planar component by micromachining.

The invention advantageously modifies the gas flow switching device described in U.S. Pat. No. 6,447,581 B2 by integrating two parallel simple open/close valves into the first gas passage in the planar component. The eluate from the first column is diverted from the second gas passage into the connecting gas passage toward the second separation column only when both valves are closed. Both valves are controlled to switch with a time difference that defines the injection pulse width. One of the valves is responsible for the start of the injection pulse and the other for the end of the injection pulse. Consequently, the mass inertia of the valves plays a secondary role for the injection pulse width. Furthermore, due to the fact that the open/close valves are integrated in the MEMS planar component, very short gas path between the valves and the point where the connecting gas passage branches off from the second gas, passages can be realized so that the peak from the first column can be sampled with minimal time delay.

The valves may be configured to be electromechanically actuated, e. g., by solenoids or piezoelectric elements integrated in or mounted on the planar component.

In another preferred embodiment, the valves are configured to be pneumatically actuated via pneumatic connections in the planar component. This leads to a very simple and inexpensive design of the planar component in the form of a passive component having nothing other than gas connections.

The valves are preferably of a snap-action type, where the valve body, such as a membrane, is deflectable from a stable position, where the valve is open to a metastable position, and where the valve is closed. This allows injection pulses with sharp front and rear edges.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The invention will now be described in greater detail by way of example and with reference to the drawing figures in which.

DETAILED DESCRIPTION OF THE PREFERRED EMBODIMENTS

Figure 1:
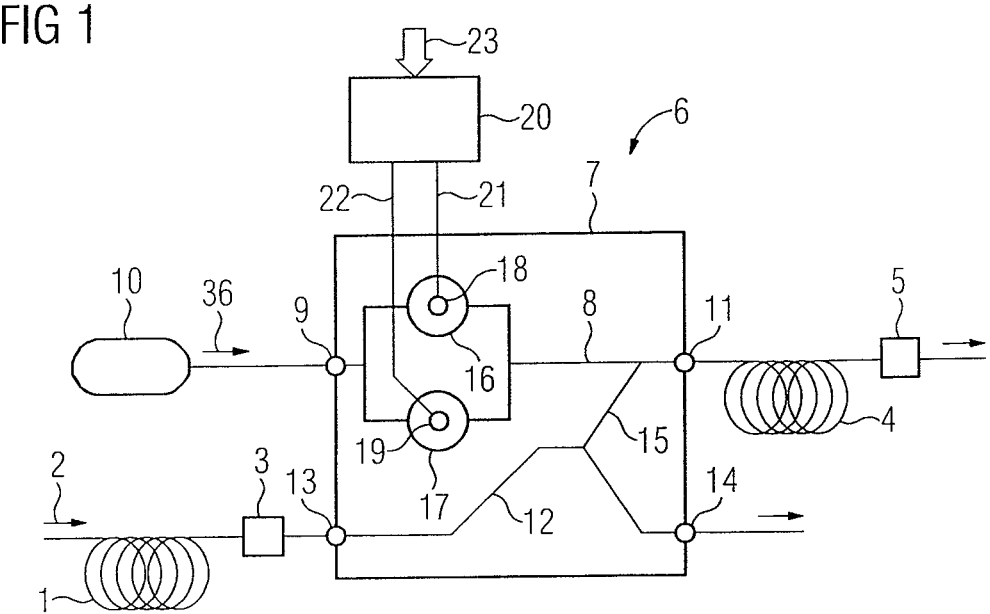
FIG. 1 illustrates an exemplary block diagram of the gas chromatograph in accordance with an embodiment of the invention.

In the following description, like reference numerals designate like parts or elements.

FIG. 1 illustrates a simplified block diagram of a comprehensive two-dimensional gas chromatograph, where only parts relevant to the embodiment of the present invention are illustrated.

The gas chromatograph comprises a first separation column 1 through which a predetermined metered quantity of a gaseous sample 2 in the form of a short plug is fed via a carrier gas. The separation column 1 is configured to separate the sample components contained in the sample 2 as they flow through the column 1 so that the individual sample components arrive in succession at a detector 3 at the end of the column 1. For each detected component, the detector 3 supplies a detector signal in the form of a chromatographic peak, which is analyzed for quantitative determination of the component. The term peak is often, and also here, used for both the detector signal and the corresponding eluate emerging from the separation column 1. Unresolved peaks may overlap, partially or completely, compromising their identification and quantification.

In order to separate and analyze each chromatographic peak or selected peaks for a second time by a second, such as fast-elution, separation column 4 and detector 5, a modulator 6 is positioned between the columns 1 and 4. The modulator 6 is based on valve operation and rapidly samples chromatographic peaks eluting from the first column 1 into the second column 4.

The modulator 6 comprises a planar component 7 in which different gas passages are formed by micromachining, such as etching techniques. The gas passages consist of channels that have the same inner diameter as that of the second separation column 4. A first gas passage 8 has a first inlet end or port 9 to which a carrier gas source 10 is connected, and a first outlet end 11 to which the second separation column 4 is connected. A second gas passage 12 has a second inlet end 13 to which the first separation column 1 followed by the detector 3 is connected, and a second outlet end 14 that serves as a gas exhaust port. The first and second gas passages 8 and 12 communicate with each other via a connecting gas passage 15. The connecting gas passage 15 branches off, at an obtuse angle, from the portion of the second gas passage 12 that comes from the second inlet end 13. At this branch point, the second gas passage 12 continues at the same angle in another direction, so that the connecting gas passage 15 and the continuation of the second gas passage 12 form a symmetrical branching fork.

Two individually controllable open/close valves 16, 17, which are formed in the planar component 7 by micromachining, are arranged in parallel connection in the first gas passage 8 between the first inlet port 9 and the branch-off of the connecting gas passage 15. In the illustrated example, the valves 16, 17 are configured to be pneumatically actuated via pneumatic connections 18, 19 in the planar component 7. The valves 16, 17 are controlled by a controller 20 via pneumatic lines 21, 22. The pneumatic controller 20 may include electromechanically actuated valves that are controlled in accordance with a control scheme 23 provided by a higher-level control system (not shown) of the gas chromatograph.

Figure 2:
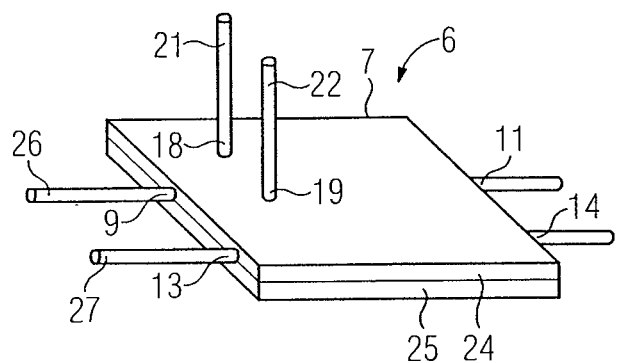
FIG. 2 illustrates a view of a first embodiment of the modulator as a part of the gas chromatograph.

FIG. 2 illustrates a view of the planar component 7 of the modulator 6. The planar component 7 comprises two plates 24, 25 that are positioned on top of one another and joined together. Congruent channels, which have respective semicircular cross sections, are formed on those sides of the two plates 24, 25 that face one another. These channels form the gas passages 8, 12, 15 (FIG. 1) and the inlet and outlet ends 9, 11, 13, 14 at their lateral exit points from the plates 24, 25. At the inlet and outlet ends 9, 11, 13, 14, the cross sections of the gas passages 8, 12 may be enlarged to accommodate capillaries such as capillary 26 from the carrier gas source 10 or capillary 27 from the first column 1. This also applies accordingly to the pneumatic connections 18, 19 and pneumatic lines 21, 22.

Figure 3:
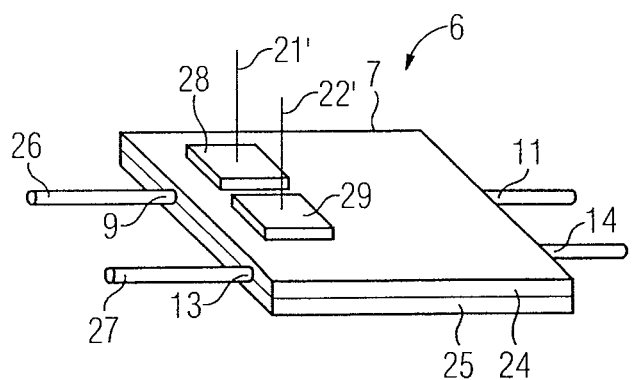
FIG. 3 illustrates a view of a second embodiment of the modulator.

FIG. 3 illustrates another example of the planar component 7, where the valves 16, 17 are electromechanically actuated by solenoids or piezoelectric elements 28, 29 integrated in or mounted on the planar component 7 and controlled by the now electronic controller 20 (FIG. 1) via electric signal lines 21', 22'.

Figure 4:
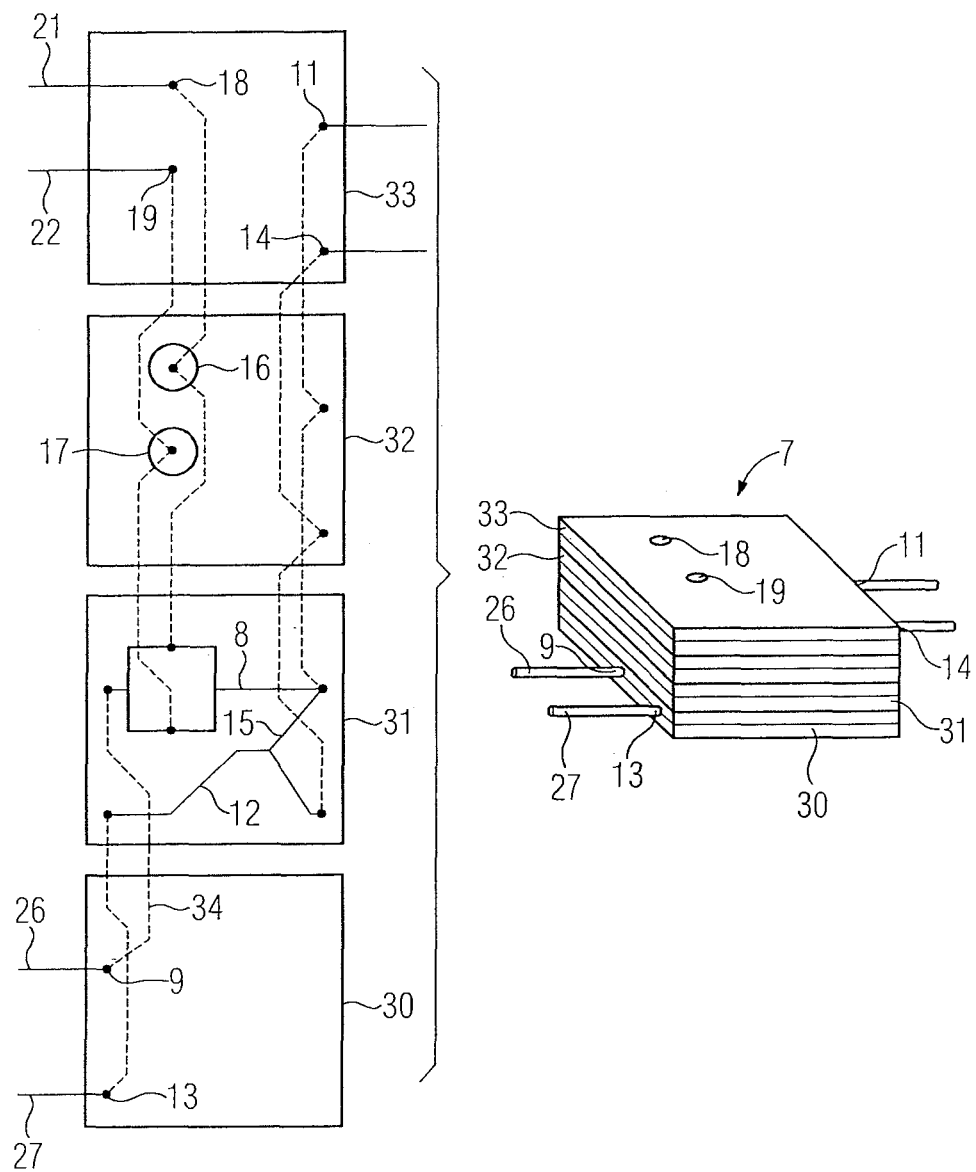
FIG. 4 illustrates a block diagram and view of another exemplary embodiment of the modulator.

FIG. 4 illustrates on the left-hand side a block diagram and on the right-hand side a view of yet another embodiment of the planar component 7 that comprises different double plates 30, 31, 32, 33 assembled into a stack. The two outer double plates 30, 33 feature all fluidic ports or connections 9, 13, 11, 14, 18, 19 and electrical connections for the signal lines 21', 22' (FIG. 3) if the valves 16, 17 are electromechanically actuated. The double plate 32 contains the gas passages 8, 12, 15. The double plate 33 contains the valves 16, 17. As indicated by dashed lines 34, fluidic connection between the different double plates 30, 31, 32, 33 is established by vertical channels.

Figure 5:
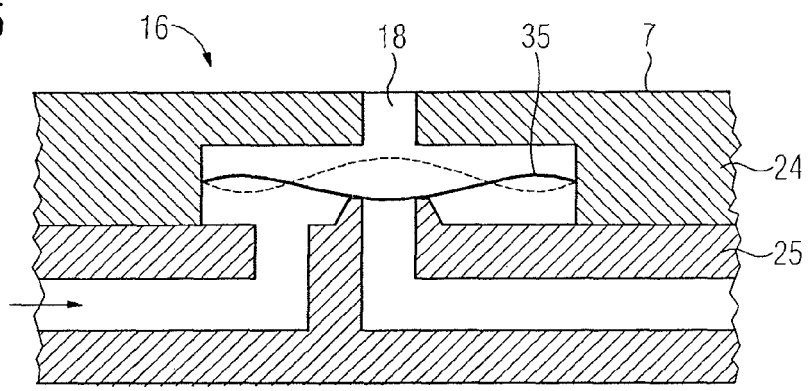
FIG. 5 illustrates an exemplary embodiment of one of two open/close valves as a part of the modulator.

FIG. 5 illustrates in a simplified form an example of the open/close valve 16 that is representative for both valves 16, 17. The valve 16 is formed in the planar component 7 by micromachining and has a valve body 35, here in the form of a membrane, which is deflectable from a stable position at which the valve 16 is open to a metastable position where the valve 16 is closed. The valve 16 is pneumatically actuated via the pneumatic connection 18 in the planar component 7.

Referring again to FIG. 1, when one or both of the valves 16, 17 are open, carrier gas flows through the first gas passage 8 to the second separation column 4. A small percentage of the carrier gas 36 flows into the connecting gas passage 15 and prevents the eluate flowing in the second gas passage 12 from entering the connecting gas passage 15. When both valves 16, 17 are closed, the eluate is diverted from the second gas passage 12 into the connecting gas passage 15 and reaches the second separation column 4 via the first gas passage 8.

Figure 6:
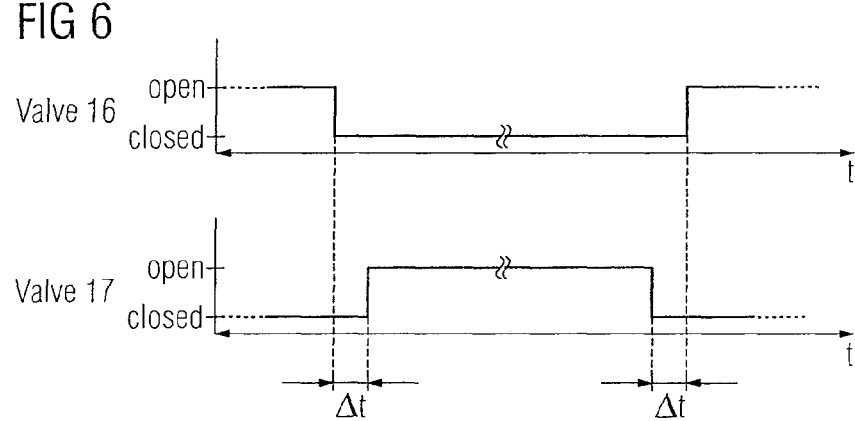
FIG. 6 illustrates a first example for controlling the valves.
Figure 7:
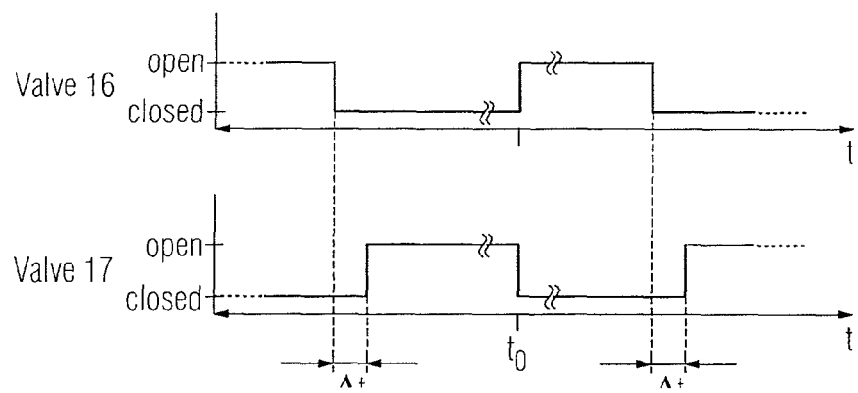
FIG. 7 illustrates a second example for controlling the valves.

FIGS. 6 and 7 illustrate two examples for controlling the valves 16, 17. The valves 16, 17 are controlled such that one valve, e. g., valve 16, initially switches from open to closed while the other valve 17 is closed, and after a predetermined time difference $\Delta t$ the other valve 17 switches from closed to open. The time difference $\Delta t$ defines the pulse width of the injection of the eluate from the second gas passage 12 into the connecting gas passage 15. In the example of FIG. 6, the switching status of each valve is maintained after each injection so that the responsibility for the start (or the end) of the injection pulse alternates between the valves 16, 17. In the example of FIG. 7, the switching status of each valve is changed at any time $t_0$ between two successive injections so that the responsibility for the start or the end of the injection pulse remains with the respective valves 16, 17.

The present invention may be embodied in other specific forms without departing from its spirit or essential characteristics. The described embodiments are to be considered in all respects only as illustrative and not restrictive.

Thus, while there have shown, described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements which perform substantially the same function in substantially the same way to achieve the same results are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A comprehensive two-dimensional gas chromatograph, comprising:
 a first separation column;
 a second separation column; and
 a modulator controlled by a controller for sampling a chromatographic peak eluting from the first separation column into the second separation column;
 wherein the modulator comprises:
  a planar component including:
   a first gas passage having a first inlet end to which a carrier gas source is connected and a first outlet end to which the second separation column is connected;

a second gas passage having a second inlet end to which the first separation column is connected and a second outlet end;
a connecting gas passage between the first and second gas passages; and
two individually controllable open/close valves arranged in a parallel connection in the first gas passage between the first inlet end and a branch-off point of the connecting gas passage from the first gas passage, the first, second and connecting gas passages and the open/close valves being formed in the planar component by micromachining;
wherein the controller is configured to start each sample event by controlling one of the open/close valves from open to close when another of the open/close valves is closed and to stop the sample event by controlling the other of the open/close valves to open.

2. The gas chromatograph of claim 1, wherein the open/close valves are each configured to be electromechanically actuated.

3. The gas chromatograph of claim 1, wherein the open/close valves are each configured to be pneumatically actuated via pneumatic connections in the planar component.

4. The gas chromatograph of claim 1, wherein the open/close valves each have a valve body which is deflectable from a stable position at which a valve is open to a metastable position at which the valve is closed.

5. The gas chromatograph of claim 1, wherein all gas passages have the same inner diameter as that of the second separation column.

6. A modulator for sampling a chromatographic peak eluting from a first separation column into a second separation column of a comprehensive two-dimensional gas chromatograph, the modulator comprising
a planar component including:
a first gas passage having a first inlet end for connection of a carrier gas source and a first outlet end for connection of the second separation column;
a second gas passage having a second inlet end for connection of the first separation column and a second outlet end;
a connecting gas passage arranged between the first and second gas passages;
two individually controllable open/close valves arranged in a parallel connection in the first gas passage between the first inlet end and a branch-off point of the connecting gas passage from the first gas passage, the first, second and connecting gas passages and valves being formed in the planar component by micromachining.

7. The modulator of claim 6, wherein the open/close valves are each configured to be electromechanically actuated.

8. The modulator of claim 7, wherein the open/close valves each have a valve body which is deflectable from a stable position at which a valve is open to a metastable position at which the valve is closed.

9. The modulator of any of claim 7, wherein all gas passages have the same inner diameter as that of the second separation column.

10. The modulator of claim 6, wherein the open/close valves are each configured to be pneumatically actuated via pneumatic connections in the planar component.

11. The modulator of claim 10, wherein the open/close valves each have a valve body which is deflectable from a stable position at which a valve is open to a metastable position at which the valve is closed.

12. The modulator of any of claim 10, wherein all gas passages have the same inner diameter as that of the second separation column.

13. The modulator of claim 6, wherein the open/close valves each have a valve body which is deflectable from a stable position at which a valve is open to a metastable position at which the valve is closed.

14. The modulator of any of claim 13, wherein all gas passages have the same inner diameter as that of the second separation column.

15. The modulator of any of claim 6, wherein all gas passages have the same inner diameter as that of the second separation column.

\* \* \* \* \*